United States Patent [19]

Baker

[11] Patent Number: 4,587,212

[45] Date of Patent: May 6, 1986

[54] IMMUNOASSAY

[75] Inventor: Terence S. Baker, Staines, England

[73] Assignee: Boots-Celltech Diagnostics Limited, Slough, United Kingdom

[21] Appl. No.: 495,601

[22] Filed: May 18, 1983

[30] Foreign Application Priority Data

May 26, 1982 [GB] United Kingdom ............... 8215462

[51] Int. Cl.[4] ............... G01N 33/53; G01N 33/542; C12Q 1/38
[52] U.S. Cl. .................................. 435/7; 435/23; 436/510; 436/537; 436/814; 436/817
[58] Field of Search ........................... 435/7, 810, 23; 436/510, 537, 814, 817, 22

[56] References Cited

U.S. PATENT DOCUMENTS

| | | | |
|---|---|---|---|
| 3,817,837 | 6/1974 | Rubenstein et al. | 435/7 |
| 3,826,616 | 7/1974 | Laing | 436/817 X |
| 4,294,922 | 10/1981 | Heap | 436/817 X |
| 4,463,090 | 7/1984 | Harris | 435/7 |

FOREIGN PATENT DOCUMENTS

| | | |
|---|---|---|
| 1401297 | 7/1975 | United Kingdom . |
| 1402263 | 8/1975 | United Kingdom . |
| 2040043A | 8/1980 | United Kingdom . |

OTHER PUBLICATIONS

Chemical Abstracts, vol. 95, 1981, Abstract No. 111258w, Sauer et al.
Chemical Abstracts, vol. 95, 1981, abstract No. 2949b, Arnstadt et al.
Sauer et al, "The Use of Enzyme Immunoassay for the Measurement of Hormones with Particular Reference to the Determination of Progesterone in Unextracted Whole Milk, " in: Wardley et al, The ELISA: Enzyme Linked Immunosorbent Assay in Veterinary Research and Diagnosis, (Boston, Martinus Nijhoff, 1982) pp. 271–301.

*Primary Examiner*—Robert J. Warden
*Assistant Examiner*—Randall E. Deck
*Attorney, Agent, or Firm*—Cushman, Darby & Cushman

[57] ABSTRACT

There is described an enzyme immunoassay for measuring the concentration of an analyte in a sample wherein the substrate for the enzyme forms at least a part of the sample. In a particular embodiment the sample comprises or consists of a milk sample and the enzyme is an enzyme capable of clotting milk. An example given of such an enzyme is chymosin. The assay described may be used to measure the concentration of progestagens or oestrogens in milk using the techniques of heterogeneous or homogeneous enzyme immunoassay. The results of such an assay give an indication of the fertility of a milk producing domestic animal (e.g. a cow) and may be used to diagnose pregnancy of such an animal. Particular compounds for use in the assay are described, as is a kit of reagents for use in the assay.

12 Claims, 3 Drawing Figures

FIG. 1

FIG. 2

|  | CONJUGATE DOUBLING DILUTIONS | | | | | | | | | | | | ANTIBODY | PROGESTERONE 0·1 nmol/ml |
|---|---|---|---|---|---|---|---|---|---|---|---|---|---|---|
| | $\frac{1}{1}$ | $\frac{1}{2}$ | $\frac{1}{4}$ | $\frac{1}{8}$ | $\frac{1}{16}$ | $\frac{1}{32}$ | $\frac{1}{64}$ | $\frac{1}{128}$ | $\frac{1}{256}$ | $\frac{1}{502}$ | $\frac{1}{1024}$ | $\frac{1}{2048}$ | | |
| | ⊗ | ⊗ | ⊗ | ⊗ | ⊗ | ⊗ | ⊗ | ⊗ | ⊗ | ○ | ○ | ○ | − | − |
| | ⊗ | ⊗ | ⊗ | ⊗ | ⊗ | ⊗ | ⊗ | ⊗ | ⊗ | ○ | ○ | ○ | | |
| | ⊗ | ⊗ | ⊗ | ⊗ | ⊗ | ⊗ | ⊗ | ⊗ | ○ | ○ | ○ | ○ | + | − |
| | ⊗ | ⊗ | ⊗ | ⊗ | ⊗ | ⊗ | ⊗ | ⊗ | ○ | ○ | ○ | ○ | | |
| | ⊗ | ⊗ | ⊗ | ⊗ | ⊗ | ⊗ | ⊗ | ○ | ○ | ○ | ○ | ○ | + | + |
| | ⊗ | ⊗ | ⊗ | ⊗ | ⊗ | ⊗ | ⊗ | ○ | ○ | ○ | ○ | ○ | | |
| | ⊗ | ⊗ | ⊗ | ⊗ | ⊗ | ⊗ | ⊗ | ⊗ | ○ | ○ | ○ | ○ | − | + |
| | ⊗ | ⊗ | ⊗ | ⊗ | ⊗ | ⊗ | ⊗ | ⊗ | ○ | ○ | ○ | ○ | | |

FIG. 3

IMMUNOASSAY

The present invention relates to an enzyme immunoassay.

The general concept of enzyme immunoassay is described in many publications. For a general review see "Immunoassays: Clinical Laboratory Techniques for the 1980's, (Laboratory and Research Methods in Biology and Medicine Vol. IV) ed. Nakamura R., Dito W. R., Rucker E. S. III published by A. R. Liss (1980)).

An enzyme immunoassay involves causing an antigenic analyte to compete in an immunochemical reaction with a known amount of antigen for a limited number of antibody binding sites. An enzyme label is used to measure the proportion of the known amount of antigen which has become bound to the antibody, making it possible to calculate the amount of analyte present in a sample with reference to a standard assay result. There are in general two types of enzyme immunoassay, classified by the method employed for detecting the proportion of the known amount of antigen which has become bound to the antibody.

In heterogeneous enzyme immunoassay either the known amount of nitrogen or the antibody may be immobilised upon a solid phase. The other is labelled with an enzyme. After equilibration with a sample solution containing an antigenic analyte the solid phase may be physically removed from the sample solution and may be washed. A substrate of the enzyme label may then be placed in contact with the solid phase in order to estimate the amount of antibody bound to the known amount of antigen. An advantage of this type of enzyme immunoassay is that the physical separation and washing steps tend to increase the assay accuracy by removing extraneous substances introduced from the sample.

A disadvantage of heterogeneous enzyme immunoassay is that the separation step is time consuming and requires a certain degree of manipulative skill.

In homogeneous enzyme immunoassay the measurement of the proportion of the known amount of antigen which has become bound to antibody relies upon a change in specific enzyme activity when an antibody binds to an enzyme labelled antigen. In homogeneous enzyme immunoassay a hapten (an antigenic molecule) is attached to an enzyme in a position relative to an active site of the enzyme such that its catalytic activity upon its substrate is unimpaired. In use, antibody binds to the hapten and by this binding reduces or destroys the specific activity of the enzyme. The modulation of enzyme activity is thought to be caused either by steric hindrance, the antibody physically preventing the substrate engaging the active site of the enzyme, or in some cases by restriction in the conformational flexibility of the enzyme, thereby preventing activity. There are some examples of homogeneous enzyme immunoassay in which the hapten, when attached to the enzyme, impairs the enzymes specific activity. The binding of an antibody to the hapten then reactivates the enzyme.

British patent specification 1401297 describes a homogeneous enzyme assay, in which the binding of a receptor to an enzyme-bound ligand reduces to some extent the specific activity of the enzyme. The specification describes in particular certain forms of homogeneous enzyme immunoassay. The assays described are designed to detect drugs or narcotics in body fluids such as saliva, blood or urine. In addition applications are described in which the assay is used to detect the presence of various substances which are produced naturally by the body. A typical test protocol described in British patent specification 1401297 involves the mixing of a urine sample suspected of containing a drug with an antibody to the drug and an enzyme-labelled drug molecule. Once a competitive equilibrium has been reached this mixture is then added to a separate substrate upon which the enzyme employed has a catalytic effect. A comparison of the relative effect of the enzyme upon the substrate with and without the urine sample allows the presence of the drug to be detected.

A common feature of the known enzyme immunoassay techniques is the use of an enzyme having activity to a substrate unrelated to the sample to be analysed. Indeed in many cases the substrate itself requires careful preparation and the analysis of the enzymic reaction needs careful interpretation. This tends to complicate the assay protocol and renders it time-consuming and manipulatively complex.

According to the present invention we provide an enzyme immunoassay for measuring the concentration of an analyte in a sample wherein the substrate for the enzyme forms at least a part of the sample.

Preferably we provide an enzyme immunoassay for measuring the concentration of an antigenic analyte in a sample comprising or consisting of milk wherein the enzyme label is an enzyme capable of clotting milk. The term "measuring" as used herein is to be taken to include both making a quantitative measurement of the concentration of an analyte in a sample and detecting whether an analyte is present in a sample in a concentration above or below a predetermined concentration. Preferably the enzyme is chymosin but it may be any other proteolytic enzyme capable of clotting milk, for example pepsin or chymosin analogues produced from microbial sources.

Chymosin is one of a number of proteolytic enzymes secreted by the fourth stomach (abomasum) of unweaned calves. It is the active ingredient of rennin (also known as rennet) and has, for hundreds of years, been used in the production of cheese. The natural substrate of chymosin is the protein casein which is the major solid component of milk. In milk, casein exists as a stable colloid of casein molecules. The addition of chymosin to milk catalyses the cleavage of casein to form proteins which are not stable as a colloid. The cleavage results in an agglutination of the protein molecules; an effect which may be observed macroscopically as clotting.

Recent advances in recombinant DNA techniques have now made available bacterially produced chymosin which may be used in the assay of the present invention (see our copending British patent application 2100737A).

The enzyme immunoassay of the invention may be a heterogeneous enzyme immunoassay but is preferably a homogeneous enzyme immunoassay.

The milk may be the milk of any mammal but is preferably the milk of a domestic milk-producing animal such as a cow, a sheep or a goat and is most preferably the milk of a cow.

The economics of dairy farming require the production of one calf per cow per year. This is necessary in order to ensure a satisfactory and constant supply of milk from a dairy herd. The calving index of a cow is the number of days that pass between successive calvings. Thus the ideal calving index is 365 days and extensions beyond this are likely to affect adversely the profitability of a cow. It is essential to good herd management that the correct time is chosen for insemination and that a check is available subsequently to ensure that conception has occurred.

Traditionally the correct time for arranging for insemination of a cow was judged by the herd manager on the basis of the behaviour of the cow. The diagnosis of pregnancy relied either upon a study of the cows subsequent behaviour or upon a rectal examination by a veterinary surgeon some 10 to 15 weeks after insemination. The necessary delay before making a physical examination often is considerable. These traditional methods are still extensively used today.

It is known that the level of progestagen in the milk of lactating dairy cows reflects ovarian activity. The cow is a polyoestrus animal and ovulates spontaneously in an oestrus cycle having a period of approximately twenty one days. The level of a particular progestagen, progesterone, in milk varies cyclically over the period between successive ovulations. The concentration of progesterone in a cow's milk builds up gradually after oestrus from a very low level to a plateau of about 25 ng/ml milk and drops sharply to a very low level immediately before the next ovulation. It is further known that if a successful insemination is carried out on the day of oestrus, the level of progesterone in milk remains high throughout the pregnancy.

British patent specification 1402263 describes a method of diagnosing pregnancy in an inseminated milk-producing domestic animal in which an assay for progestagen is carried out on the milk of the animal in order to ascertain whether the progestagen concentration is varying cyclically or is fixed at high value. The latter result is indicative of pregnancy.

The methods of assay described in British patent specification 1402263 are competitive protein binding assay and radioimmunometric assay. Both these assays require skilled work and specialised equipment, and often involve considerable time delays.

An alternative method of diagnosing pregnancy in cows is described in British patent specification 2040043. The level of an oestrogen metabolite, oestrone sulphate, in milk increases gradually during pregnancy and gives a further indication of successful insemination. British patent specification 2040043 describes a method of measuring the level of oestrone sulphate in milk using an enzyme-linked immunoassay involving a colourimetric determination of end point. Such an assay involves less skill on the part of the operator but nevertheless is time-consuming and complex.

Many countries now have commercial laboratories which will assay milk samples for progesterone. The technique most commonly used by such laboratories is radioimmunoassay. This inevitably involves delay, and if the assay is required for the purposes of detecting oestrus the result of the assay may arrive too late for successful insemination.

There is therefore a great need in the dairy industry for a simple and effective assay for progestagens, progestagen metabolites, oestrogens and oestrogen metabolites such that the herd manager can perform a 'cow side' test for oestrus or for pregnancy. In a preferred form of the present invention we provide such an assay.

Accordingly we provide an enzyme immunoassay for measuring the amount of a steroid selected from a progestagen, a progestagen metabolite, an oestrogen, and an oestrogen metabolite, in a sample containing or consisting of milk wherein the enzyme label is an enzyme capable of clotting milk. Preferably the steroid is progesterone or oestrone sulphate.

A number of diagnostic tests to be applied to cows are made possible by the assay of the present invention.

According to a preferred method the onset of oestrus in a milk-producing domestic animal such as a cow, a sheep or a goat is detected by monitoring the level of progesterone in the milk of the animal using the assay of the present invention. The assay may be used, for example, to indicate when the level of progesterone in the milk of the animal falls below a predetermined value. In the general method, using a homogeneous enzyme immunoassay, a molecule of progesterone (or a molecule having at least one antigenic determinant in common with progesterone) is chemically bonded to a chymosin molecule at a point adjacent the active site of chymosin. In performing the assay a mixture is prepared consisting of the progesterone-chymosin conjugate molecule, a limiting amount of antibody to progesterone and a sample of milk including inter alia the progesterone and casein. A competitive equilibrium is established in which the free progesterone and the progesterone-chymosin conjugate molecule compete for the limiting amount of antibody. If the progesterone is absent or present only in low concentration in the milk sample a significant fraction of the antibody will bind to the progesterone-chymosin conjugate. The action of the chymosin will be impaired and no clotting of the milk will be observed. In the alternative, if progesterone is present in the milk sample a significant fraction of the antibody will become bound to the progesterone in the sample. This will result in the presence of non-immunocomplexed progesterone-chymosin conjugate in the sample, the chymosin will therefore be active and clotting of the milk sample will be observed. The sensitivity of the assay may be adjusted by altering the concentrations of the various reagents used in the assay. It is also possible to adjust the sensitivity of the assay by changing the order in which the reagents are admixed. For example, the addition of the antibody to the milk sample before the progesterone-chymosin conjugate will affect the sensitivity. In general a level of progesterone below 4 ng/ml is indicative of the onset of oestrus.

In a practical situation the dairyman can take a sample from a cow whilst still in the dairy. The sample may be placed in a suitable receptacle and the various reagents may be added. Following agitation the presence or absence of clotting may be observed. When using the assay for progesterone a change in the result from clotting to non-clotting may be taken as an indication of the onset of oestrus, indicating as it does that the concentration of progesterone in the cow's milk has fallen below a predetermined level.

We further provide a method for detecting pregnancy in a milk-producing domestic animal, comprising using an enzyme immunoassay according to the invention to monitor the concentration of progesterone in the milk of the animal, pregnancy being indicated by the lack of a drop in the concentration of progesterone below a predetermined concentration at a time when oestrus would be expected.

We further provide a method for detecting pregnancy in a milk-producing domestic animal, comprising using an enzyme immunoassay according to the invention to monitor the concentration of oestrone sulphate in the milk of the animal, pregnancy being indicated by a concentration of oestrone sulphate above a predetermined concentration.

Preferably the above pregnancy tests are carried out in relation to a cow.

In a further aspect of the invention we provide a steroid-chymosin conjugate molecule wherein the specific enzyme activity of the chymosin may be modulated by the formation of an immunochemical bond between the steroid and an antibody to the steroid. The modulation of specific enzyme activity of the chymosin part of the conjugate molecule may increase or decrease the specific enzyme activity. Preferably, however, activity modulation decreases the specific enzyme activity of the chymosin part of the conjugate molecule. The steroid part of the conjugate molecule may be any molecule having the steroid fused ring system. In producing suitable conjugates which exhibit modulation of enzyme activity it is necessary to attach the steroid adjacent the active site of the enzyme. Ideally one steroid would be attached in such a position. In practice, it is difficult to arrange for a specific point of coupling upon the chymosin. The steroids may conveniently be attached to lysine groups on the chymosin and in order to produce conjugates capable of modulation it is generally necessary to bind more than one steroid molecule to each chymosin molecule. Preferably 1 to 10 steroid molecules are attached to one chymosin molecule. Most preferably only one steroid molecule is attached to each chymosin molecule as each additional steroid molecule reduces the extent to which the activity of chymosin is modulable. More than one steroid may be attached to the chymosin molecule to produce a conjugate molecule of the invention. A suitable linking molecule may be employed to ensure that the steroid and the chymosin are held at an optimum distance for maximum activity modulation. An especially preferred linking module is a heterocycle derived from a glucuronide sugar group. The following conjugates are particularly preferred:

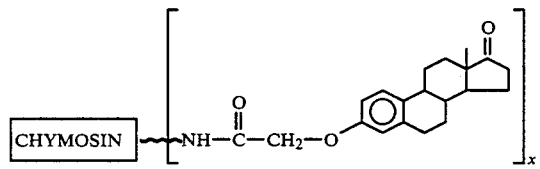

wherein x is 1 to 10.

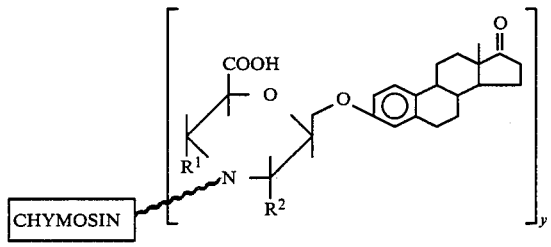

wherein y is 1 to 10, and $R_1$ and $R_2$ are different and are —H or —OH.

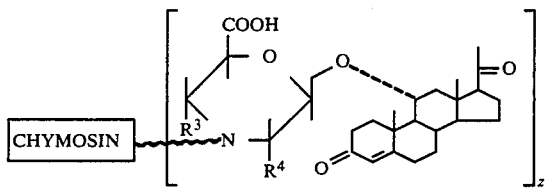

wherein z is 1 to 10, $R_3$ and $R_4$ are different and are —H or —OH.

Finally we provide a kit for performing a preferred enzyme immunoassay of the present invention. The kit comprises, separately, or in a combination, a steroid chymosin conjugate as described above and an antibody to the steroid.

Some embodiments of the present invention are now described as examples, with reference to the accompanying drawings in which:

Figures 1, 2:
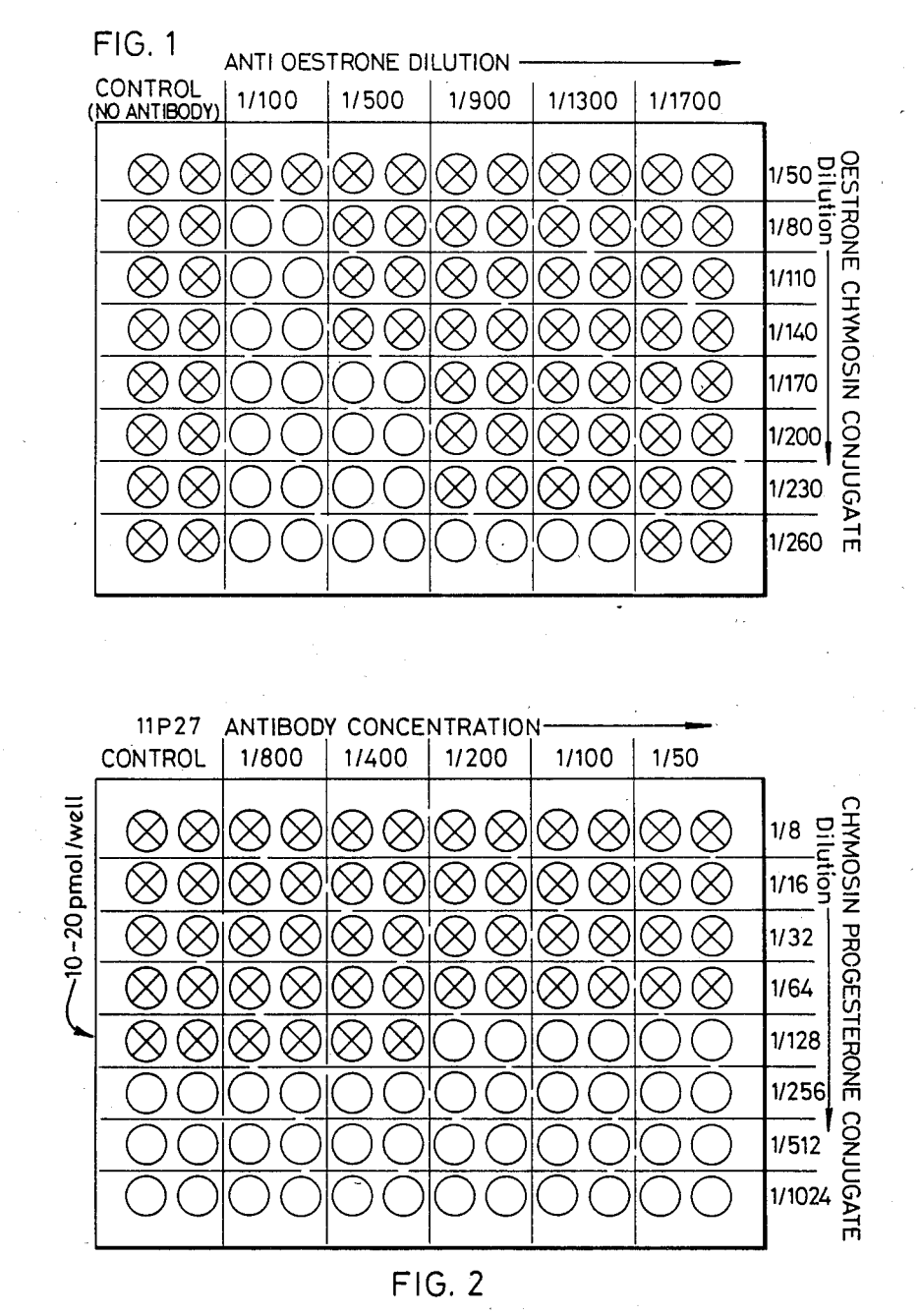

FIG. 1—shows the results of a 'checkerboard' titration on a microtiter plate indicating the effect upon milk samples of various dilutions of anti-oestrone in combination with various dilutions of oestrone-chymosin conjugate.

FIG. 2—shows the results of a 'checkerboard' titration on a microtiter plate indicating the effect upon milk samples of various dilutions of anti-progesterone in combination with various dilutions of progesterone-chymosin conjugate.

FIG. 3—shows the results of a 'checkerboard' titration on a microtiter plate indicating modulation of enzyme activity of a chymosin-progesterone conjugate by anti-progesterone.

In all the Figures the circles represent wells in the microtiter plate. Where a cross appears within a circle a milk clot was evident.

A. MATERIALS

1. Antibodies

Polyclonal antibody to oestrone-3-glucuronide was obtained from Dr. Samarajeewa of the Courtauld Institute of Biochemistry, Cleveland Street, London W1, England. It had been raised against the immunogen oestrone-3-glucuronide-bovine serum albumin according to the method of Samarajeewa and Kellie ((1975) Biochemical J. 151 369–376). This antiserum exhibited a high cross-reactivity to both oestrone and its metabolite oestrone-3-sulphate, and thus was chosen as a useful reagent for the immunoassay of oestrone-3-sulphate in milk.

Polyclonal antibody to progesterone was obtained from the Milk Marketing Board, Veterinary Laboratories, Cleeve House, Lower Wick, Worcester, England. It had been raised against the immunogen progesterone-11α-hemisuccinyl-bovine serum albumin and cross reacted strongly with progesterone and its metabolite progesterone-11α-glucuronide. (Corrie. J.E.T. (1982) J. Immunol. Methods 51 pp. 159–162).

Monoclonal progesterone antibodies were obtained from Dr. Wang of the Imperial Cancer Research Fund Laboratories, Lincolns Inn, London, England. They had been raised against the immunogen progesterone-11αsuccinyl-bovine serum albumin according to the method of Fantl, V. E., Wang, D. Y. and Knyba ((1982) J. Steroid Biochem. 17 pp. 125–130). Antisera described in this publication which were found to be useful in this invention are 11P12, 11P23 and 11P27.

2. Chymosin

Calf chymosin (EC 3.4.23.4) was obtained from Sigma Chemical Co. Ltd., Fancy Road, Poole, Dorset, England.

3. Steroids

Progesterone-11α-glucuronide was prepared according to the method of Corrie J. E. T., Hunter W. M. Macpherson H. S. (Clin. Chem. (1981) 27 594–599). Oestrone, oestrone-3-glucuronide and oestrone sulphate were obtained from Sigma Chemical Co. Ltd. Oestrone-3-O-carboxymethyl ether was prepared by the method of Rao, P. N. and Moore, P. H. (Steroids (1977) 29 pp. 462–469). Tritiated oestrone-3-glucuronide was obtained from Dr. P. Samarajeewa of the Courtauld Institute of Biochemistry.

4. Milk Substrate

Substrates used to demonstrate the immunoassay principle were prepared from either commercial preparations of powdered, de-fatted milk such as MARVEL (Trade Mark) or fresh whole cows milk, obtained from cows which had recently calved (7 to 14 days post-calving) or from cows which had been observed to be at oestrus.

Substrate solutions were prepared by dissolving the powdered milk in 40 mM calcium chloride to give a concentration of 24% (w/v) or by dissolving calcium chloride crystals in whole milk to a concentration of 40 mM. In either case the substrate solutions were incubated at 37° C. for at least 15 minutes prior to use.

5. Assay Buffer 0.05 M sodium phosphate buffer at pH 6.3., containing 0.03% (w/v) bovine serum albumin.

6. Microtiter Plates

The immunoassay system was demonstrated by carrying out the assay in the wells of polyvinylchloride, u-well, microtiter plates. There were obtained from Dynatech Limited, Duax Road, Billinghurst, Sussex, England.

7. Incubator

The assays to be described were carried out at 37° C. using a microtiter plate incubator (Dynatech Ltd.).

8. Other Reagents

These were obtained from Sigma Chemical Co. Ltd.

B. METHODS

1. Purification of antibodies

Polyclonal and monoclonal antisera were purified by precipitation with polyethylene glycol. To 1 ml of antibody solution was added an equal volume of 20% (w/v) solution of polyethylene glycol (M.W. 3000) in 0.1 M phosphate buffer pH 6.5. The addition was made at room temperature slowly over a 2 minute period with continual stirring. After 30 minutes the resulting precipitate was pelleted by centrifugation at 3000 r.p.m. for 35 minutes. The supernatant was discarded and the tube containing the pellet was inverted and left to drain overnight at 4° C. The pellet was dissolved in assay buffer and used at a suitable dilution dependant upon the experiment being conducted.

2. Preparation of conjugates

Three different coupling reactions of steroids to chymosin are described. In each case 'n' steroid molecules were attached to each chymosin molecule.

(i) Conjugation of oestrone-3-carboxymethyl ether to chymosin

Oestrone-3-carboxymethyl ether (2.6 mg) in 95% aqueous dioxane (0.05 ml) was treated with ethyl-3-(3-dimethyl) amino propyl) carbodiimide (2.14 mg) (EDC) and N-hydroxysuccinimide (1.26 mg) (NHS). The mixture was kept at room temperature for 12 hours and then water (0.5 ml) was added and the solution was extracted with ethyl acetate (3×1 ml). The ethyl acetate extract was washed with water and the organic phase removed in vacuo. The resulting solid was stored, dessicated, at −20° C. until required.

Oestrone-3-carboxymethylether-N-hydroxy succinimide ester (1.4 mg) in methylene chloride (0.5 ml) was placed in a glass reaction vessel and the solvent evaporated under a stream of nitrogen. A solution of chymosin (3.5 ml at 1.1. mg/ml) in 0.1 M phosphate buffered saline, pH 7.5, was added to the steroid derivative and the reaction vessel was agitated for 18 hours at 4° C. The reacted enzyme was separated from excess steroid by gel filtration using 2 G-25 Sephadex (Trade Mark) PD10 columns (Pharmacia Ltd., Pharmacia House, Midsummer Boulevard, Milton Keynes, MK9 3HP, England). The eluent used was assay buffer. The yield of protein was about 100% but had 62% of its original milk clotting activity. The overall reaction scheme was as follows:

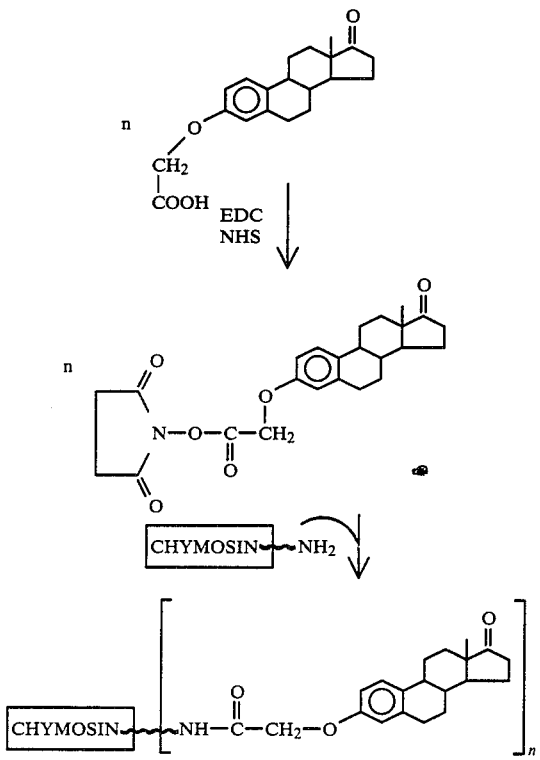

(ii) Conjugation of oestrone-3-glucuronide to chymosin

Oestrone-3-glucuronide sodium salt (5.2 mg) and tritiated oestrone-3-glucuronide (20×10⁶ d.p.m. (disintegrations per minute) in 200 μl ethanol) were dissolved in 1 ml of 0.1 M sodium acetate buffer (pH 5.0 ) A 0.2 M sodium m-periodate solution (0.5 ml) was added and the mixture was incubated in the dark at 4° C. for 12 hours. Ethylene glycol (0.2 ml) was added and after 30 minutes the reaction mixture was diluted with 10 ml water.

The resulting steroid dialdehyde was extracted with ethyl acetate (4×20 ml) and the combined extracts were then washed with water (10 ml) and dried over anhydrous sodium sulphate. After filtering, the solvent was removed in vacuo. The yield based on tritium recovery was 50%. The residue was dissolved in 50 mM phosphate buffer pH 7.6 (2 ml).

Chymosin (10 mg) was dissolved in 0.05 M phosphate buffer, pH 6.3 (2.5 ml) and subjected to gel filtration on a G-25 PD10 column. A 35 ml fraction eluting after the void volume was collected and adjusted to pH 7.6 with dilute sodium hydroxide. The protein concentration was 1.1 mg/ml. The oxidised steroid solution (1 ml) was mixed with the chymosin solution and then a sodium cyanoborohydride solution was added (3.1 mg in 0.05 ml) and the mixture was incubated at 4° C. for 12 hours.

The resulting chymosin-oestrone conjugate was purified by gel filtration using G-25 PD10 columns followed by exhaustive dialysis over 3 days against assay buffer containing a 2% charcoal suspension. It was estimated by measuring radioactivity that four steroid molecules had been incorporated per molecule of enzyme (i.e. N=4). The conjugate retained 87% of its original milk clotting activity. The overall reaction scheme was as follows: (the hydroxyl groups shown in parenthesis are alternative positions of the group)

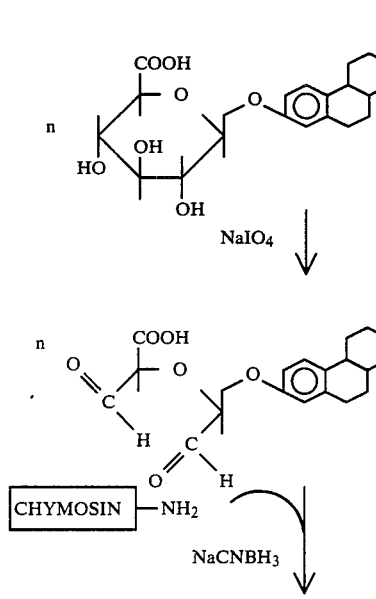

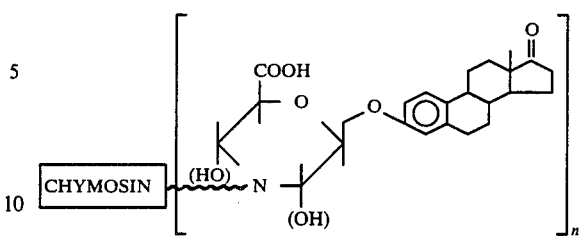

(iii) Conjugation of progesterone-11α-glucuronide to chymosin

Progesterone-11α-glucuronide (2.2 mg) was dissolved in 0.05 phosphate buffer (0.5 ml) and adjusted to pH 7.0 with dilute sodium hydroxide sodium m-periodate solution (0.2 M, 0.1 ml) was added and the solution was incubated at 20° C. for 3 hours. Ethanediol (0.02 ml) was added and after 30 minutes the solution was gel filtered using a G-10 Sephadex column (Trade Mark) (30×1 cm) and using phosphate-buffered saline (pH 7.0 as eluent.

Chymosin (6.9 mg in 3 ml assay buffer) was added to the oxidised steroid solution followed by a solution of sodium cyanoborohydride (0.62 mg in 0.05 ml). The reaction was allowed to proceed for 18 hours at 4° C. Finally the reaction mixture was dialysed against a suspension of 2% of charcoal. The overall reaction was as follows: (the hydroxyl groups in parenthesis are alternative positions of the group)

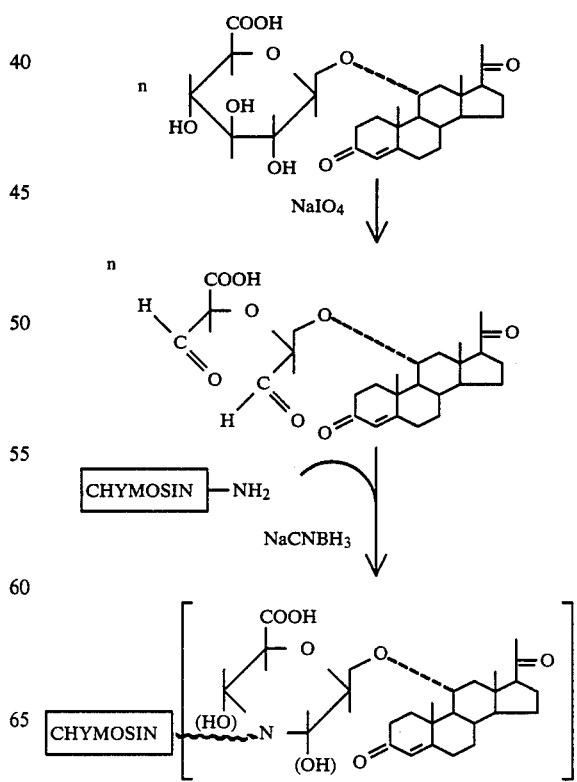

3. Testing of steroid-chymosin conjugates for milk clotting activity and for modulation of their milk clotting activity by reaction with steroid antibody Milk clotting assays were carried out for convenience in the wells of microtiter plates. After a suitable reaction time, the microtiter plates were inverted. Where clotting occurred, the clots remained in the wells of the plate; where there was no clotting, the contents of the wells were decanted.

The basic assay procedure was as follows:

50 μl of assay buffer containing the desired concentrations of steroid-chymosin conjugate and/or antibody was pipetted into the microtiter plate wells. This was followed by 50 μl of a milk substrate solution to which had been added either no steroid or a calculated amount of a progesterone (or oestrone sulphate) in order to produce a desired concentration of that steroid in the well.

The microtiter plate containing such reaction mixtures was placed in a 37° C. incubator for 1 hour. At the end of this time the plate was inverted over a sink and tapped very lightly a few times, and then placed inverted on some tissue paper. The presence of clots was readily observed and either scored on a microtiter plate diagram or alternatively the inverted plate was photocopied against a dark background.

In order to demonstrate modulation of clotting activity by reaction of antibody with steroid-chymosin conjugates and to determine optional concentrations of both reagents for use in immunoassay system, a 'checkerboard' titration of antibody against conjugate was performed.

In this type of experiment a series of steroid chymosin conjugate concentrations was added to a microtiter plate down each column of wells, usually by serial doubling dilutions as before. In the other direction, along the rows of the microtiter plate, a series of antibody concentrations was added, usually by serially diluting the antibody.

For example, in one experiment the oestrone-3-glucuronide chymosin conjugate was diluted from 1/50 (0.22 μM) to 1/260 (0.04 μM) and oestrone antibody was diluted from 1/100 (0.47 μM, polyclonal IgG fraction) to 1/1700 (see FIG. 1). Progesterone 11α glucuronide-chymosin conjugate dilutions of ½ (1.36 μM) to 1/2024 (0.011 μM) were chosen and titrated against progesterone antibody (11P27) from 1/50 (18 nM, monoclonal IgG) to 1/800 (1.11 nM) dilution (see FIG. 2). In each experiment a control where no antibody had been added was included.

4. Immunoassay system for detecting steroid in milk

From the checkerboard titration experiments antibody concentrations were selected which were capable of modulating steroid-chymosin clotting activity. At the minimal concentration of conjugate necessary for clotting in the absence of antibody, a minimal concentration of antibody was selected which was capable of abolishing clotting activity at this concentration. Experiments were set up to investigate the effect of endogenous steroid (in the milk substrate) on the modulation of clotting activity by antibody. In a specific example, (see FIG. 3) for detecting progesterone in milk an optimal monoclonal antibody (11P12) dilution was selected at 1/500. Keeping antibody concentration constant at 1/500 progesterone chymosin conjugate dilution was varied from 1/1 (10.9 μM) to 1/2048 (0.005 μM). In a parallel series of wells the added substrated solution contained 0.1 nmol/ml progesterone. Also a control series of wells was included in the plate in which antibody was absent.

In the absence of antibody the limiting concentration of progesterone-chymosin conjugate necessary for clotting was 1/256 dilution. However when antibody at 1/500 dilution was also present, clotting was abolished. The presence of 0.1 nmol/ml progesterone in the milk sample was able to reverse this modulation by antibody and restore clotting activity.

This concentration of progesterone in milk (0.1 nmol/ml) is similar to that found in milk from cows that are pregnant or those non-pregnant cows which are not at oestrus. This shows that the assay is suitable for detecting the presence or absence of pregnancy or oestrus in cows.

I claim:

1. In an enzyme immunoassay for measuring the concentration of an antigenic analyte in a milk sample wherein the enzyme labeled binding partner is introduced to said milk sample and wherein enzyme activity provides a measure of analyte concentration, the improvement wherein the enzyme is an enzyme capable of clotting milk and the substrate for the enzyme forms at least part of the milk sample.

2. An enzyme immunoassay according to claim 1 wherein the enzyme is chymosin.

3. An enzyme immunoassay according to claim 1 wherein the enzyme immunoassay is a homogeneous enzyme immunoassay.

4. An enzyme immunoassay according to claim 1 wherein the antigenic analyte is a steroid selected from the group consisting of a progestagen, a progestagen metabolite, an oestrogen and an oestrogen metabolite.

5. An enzyme immunoassay according to claim 4 wherein the antigenic analyte is progesterone.

6. An enzyme immunoassay according to claim 4 wherein the antigenic analyte is oestrone sulphate.

7. A method for detecting the onset of oestrus in a domestic milk-producing animal comprising using an enzyme immunoassay according to claim 5 to monitor the concentration of a progesterone in the milk of the animal, the onset of oestrus being indicated by a concentration of progesterone below a predetermined concentration.

8. A method for detecting pregnancy in a domestic milk-producing animal comprising using an enzyme immunoassay according to claim 5 to monitor the concentration of progesterone in the milk of the animal, pregnancy being indicated by the lack of a drop in the concentration of progesterone below a predetermined concentration at a time when oestrus would be expected.

9. A method for detecting pregnancy in a milk-producing domestic animal comprising using an enzyme immunoassay according to claim 6 to monitor the concentration of oestrone sulphate in the milk of an animal, pregnancy being indicated by a concentration of oestrone sulphate above a predetermined concentration.

10. A method according to claim 7 wherein the domestic milk-producing animal is a cow.

11. A method according to claim 8 wherein the domestic milk-producing animal is cow.

12. A method according to claim 9 wherein the domestic milk-producing animal is cow.

* * * * *